United States Patent
Kramer et al.

(10) Patent No.: US 7,591,838 B2
(45) Date of Patent: Sep. 22, 2009

(54) ORTHOPEDIC FIXATION DEVICE

(75) Inventors: Ulrich Kramer, Tuttlingen (DE); Joerg Schumacher, Tuttlingen (DE); Michael Potulski, Ohlstadt (DE); Rudolf Beisse, Seehausen (DE); Jeffrey Alan Kozak, Houston, TX (US)

(73) Assignee: Aesculap AG, Tuttlingen (DE)

( * ) Notice: Subject to any disclaimer, the term of this patent is extended or adjusted under 35 U.S.C. 154(b) by 553 days.

(21) Appl. No.: 11/070,826

(22) Filed: Mar. 1, 2005

(65) Prior Publication Data

US 2006/0004360 A1 Jan. 5, 2006

Related U.S. Application Data

(63) Continuation of application No. PCT/EP02/09878, filed on Sep. 4, 2002.

(51) Int. Cl.
*A61B 17/04* (2006.01)
(52) U.S. Cl. ...................................... 606/265
(58) Field of Classification Search ............... 606/61, 606/250–253, 260, 264–265, 267–270, 277, 606/278, 246
See application file for complete search history.

(56) References Cited

U.S. PATENT DOCUMENTS

| | | | |
|---|---|---|---|
| 5,024,213 A * | 6/1991 | Asher et al. ................. | 606/278 |
| 5,330,473 A | 7/1994 | Howland | |
| 5,474,551 A | 12/1995 | Finn et al. | |
| 5,611,800 A | 3/1997 | Davis et al. | |
| 5,643,259 A * | 7/1997 | Sasso et al. .................. | 606/61 |
| 5,676,703 A | 10/1997 | Gelbard | |
| 5,709,685 A * | 1/1998 | Dombrowski et al. ....... | 606/278 |
| 5,741,255 A | 4/1998 | Krag et al. | |
| 6,602,253 B2 * | 8/2003 | Richelsoph et al. ......... | 606/252 |
| 6,958,066 B2 * | 10/2005 | Richelsoph et al. ......... | 606/252 |
| 7,320,556 B2 * | 1/2008 | Vagn-Erik ................... | 403/385 |
| 2008/0021467 A1 * | 1/2008 | Schumacher et al. ......... | 606/61 |

FOREIGN PATENT DOCUMENTS

| | | |
|---|---|---|
| EP | 0 384 001 | 8/1990 |
| EP | 1016381 A1 * | 7/2000 |
| WO | 97/06742 | 2/1997 |

* cited by examiner

*Primary Examiner*—Eduardo C Robert
*Assistant Examiner*—Ellen Rust
(74) *Attorney, Agent, or Firm*—Lipsitz & McAllister, LLC (57) ABSTRACT

The invention relates to an orthopedic fixation device for securing a rod-like fixation element, with two clamping jaws which can be moved relative to one another and which, when brought together, clamp the fixation element between them. In order to permit space-saving configurations of a fixation device that can be introduced and operated through small orifices in the body, a cam body is provided which is mounted on the fixation device so as to be able to rotate next to the clamping jaws in the direction of tightening and which, when rotated, pushes one clamping jaw toward the other.

51 Claims, 9 Drawing Sheets

ORTHOPEDIC FIXATION DEVICE

This application is a continuation of international application number PCT/EP2002/009878 filed on Sep. 4, 2002.

The present disclosure relates to the subject matter disclosed in international application No. PCT/EP2002/09878 of Sep. 4, 2002, which is incorporated herein by reference in its entirety and for all purposes.

BACKGROUND OF THE INVENTION

The invention relates to an orthopedic fixation device for securing a rod-like fixation element, with two clamping jaws which can be moved relative to one another and which, when brought together, clamp the fixation element between them.

To fix bones or bone parts relative to one another, for example in the region of the spinal column, it is known to use rod-like fixation elements which, at different locations, are clamped between clamping jaws, and these clamping jaws are then connected by bone screws or similar fixation means to the bones or bone fragments to be fixed (WO 97/06742; U.S. Pat. No. 5,741,255; U.S. Pat. No. 5,676,703; U.S. Pat. No. 5,024,213; U.S. Pat. No. 5,474,551). Very substantial forces arise in some cases, so that these fixation devices have to be of a very stable construction. This necessarily entails that some known devices have a complicated and awkwardly shaped structure. Particularly in procedures involving minimally invasive access, it is therefore difficult to implant these fixation devices and actuate the various locking screws and other types of clamping mechanisms. In some cases, a plurality of screws or locking nuts have to be tightened (U.S. Pat. No. 5,741,255), and, in other cases, the individual parts have to be joined together in the body because the direction of screwing and the direction of insertion of the rod-like fixation elements are different (WO 97/06742; U.S. Pat. No. 5,474,551).

It is an object of the invention to construct a fixation device of the generic type in such a way that it can be easily implanted and fixed.

SUMMARY OF THE INVENTION

In an orthopedic fixation device of the type described at the outset, this object is achieved, according to the invention, by a cam body which is mounted on the fixation device so as to be able to rotate next to the clamping jaws in the direction of tightening and which, when rotated, pushes one clamping jaw toward the other clamping jaw.

With such a device, it is a simple matter to push the rod-like fixation element from above in between the two clamping jaws and then simply fix it by rotating the cam body. In this way, complicated screwing operations with a great many rotations are unnecessary, so that these procedures can also easily be performed through small openings in the body. Maneuvering of the cam body can additionally be made easier by the fact that the rotatability of the cam body is limited, for example by limit stops, in the tightening direction and/or in the release direction. On the one hand, this gives the operating surgeon an indication of whether a complete tightening or release of the cam body has taken place, and, on the other hand, this avoids overtightening, which could in some cases result in the device being damaged. This limiting action can be provided by limit stops.

In a preferred embodiment, the cam body is mounted rotatably on a rotationally symmetrical mounting body on which the clamping jaws are also held. The rotation axis of the cam body can preferably extend parallel to the axis of the rotationally symmetrical mounting body, and the rotation axis of the cam body is in particular identical to the axis of the rotationally symmetrical mounting body.

The rotationally symmetrical mounting body can, for example, have a circular cylinder configuration, but it is also possible for said mounting body to have, for example, a spherical configuration or a conical configuration. It is particularly advantageous if the mounting body is formed by the shaft of a bone screw or of a hook, since in this case it is then sufficient to push clamping jaws and cam body onto this shaft and rotate the cam body about the mounting body in order to assemble the fixation device and fix it. This fixing can constitute both a fixing against rotation and a fixing against axial movement.

It is advantageous if a support piece, which carries the two clamping jaws, is held on the rotationally symmetrical mounting body.

In a first preferred embodiment, the support piece is rigidly connected to the mounting body, and, in such a configuration, the clamping jaws can be moved relative to one another substantially only in the clamping direction.

In a preferred embodiment, however, the support piece is held on the rotationally symmetrical mounting body so as to be rotatable about the axis of symmetry of said mounting body. This affords a further possibility of adjustment, that is to say the clamping jaws can not only be drawn toward one another, but can also be rotated together about the axis of the mounting body. In this configuration, when the cam body is rotated on the mounting body, this necessarily leads not only to a clamping of the rod-like fixation element between the clamping jaws, but in addition to a securing of the support piece mounted rotatably on the mounting body, because the cam body engages against the mounting body and thus clamps the support piece relative to the mounting body.

The support piece can be pushed onto the rotationally symmetrical mounting body in the direction of the rotation axis, thus ensuring particularly simple assembly of the implant. For example, in the case of a mounting body formed by the shaft of a bone screw, it then suffices to push the support piece from above onto the bone screw, and then introduce, in the same push-on direction, a tool with which the cam body is adjusted, and only a very small opening in the body is needed for this.

In a preferred embodiment, one of the two clamping jaws is configured as a stationary clamping jaw whose spacing from the rotation axis of the cam body is substantially fixed, whereas the other one is configured as a movable clamping jaw which can be moved by the cam body toward the stationary clamping jaw.

In principle, the stationary clamping jaw can be connected rigidly to the support piece. A configuration of particular advantage, however, is one in which the clamping jaws are connected to the support piece so as to be able to pivot about a rotation axis extending parallel to the clamping direction of the clamping jaws. This affords a further possibility of adjustment, such that the direction of the rod-like fixation elements relative to the mounting body can also be adjusted. It is then advantageous if a limit stop for the stationary clamping jaw is disposed on the support piece and limits a movement of the stationary clamping jaw in the direction of the rotation axis of the clamping jaw and thus limits a movement of the stationary clamping jaw away from the rotation axis of the cam body. In such an embodiment, the clamping jaws are freely rotatable relative to the support piece about the rotation axis extending parallel to the clamping direction as long as the cam body is not tensioned. However, when the cam body is tensioned, the clamping jaws are pushed jointly against the limit stop and are thus fixed against further rotation about the rotation axis extending parallel to the clamping direction; the movable clamping jaw is then pivoted further toward the clamping jaw now fixed by the limit stop and additionally clamps the rod-like fixation element between the clamping jaws. It is thus possible, simply by tensioning the cam body, to eliminate all the degrees of freedom that the device has when the cam body is released.

The rotation axis of the clamping jaws and the rotation axis of the cam body can be located in one plane, and, in a modified embodiment, provision can also be made for the rotation axis of the clamping jaws and the rotation axis of the cam body to be laterally offset from one another. By means of these different configurations, it is possible for the implant to be adapted to the local conditions.

It is advantageous if both clamping jaws are formed by the side walls of a clamping body which has a U-shaped cross-section and whose side walls can be bent resiliently relative to one another. An especially advantageous configuration is obtained if, with the cam body released, the clamping jaws can be moved resiliently apart from one another so far that a rod-like fixation element can be pushed in between them. This allows the fixation element to be snapped in elastically between the two clamping jaws as long as the cam body has not yet been tensioned, and yet the resilient clamping jaws will fix the inserted fixation element in a provisional way, so that, although the connection does not immediately come loose, it can nevertheless still be adjusted.

It is advantageous if the pivot connection between the clamping jaws and support piece is releasable.

For example, the pivot connection can comprise two mounting members which engage behind one another in a bayonet fashion but which, in a defined angular position, do not engage behind one another and are then axially movable relative to one another. If, for example, support piece and clamping jaws are rotated through 90° relative to one another, they could be axially movable relative to one another, whereas in a parallel orientation both mounting members are secured on one another in the axial direction so that a rotation connection is then produced which cannot be released over a certain angle range, but only when the two mounting members are pivoted back into the starting position extending perpendicular to one another.

The cam body can engage directly on the movable clamping jaw, but in some cases it is advantageous if, between the cam body and the clamping jaws, there is an intermediate member which, when the cam body is rotated, is moved to a greater or lesser extent against the clamping jaws. On the one hand, this permits an adjustment in dimensions, and, on the other hand, this intermediate member can be configured in such a way that, in the case of clamping jaws that are rotatable relative to the support piece, it is possible to ensure that, in different angular positions of the clamping jaws, the cam body can transmit a tensioning or loading force to the movable clamping jaw via the intermediate member.

The intermediate member can be held movably on the support piece, and it is advantageous in particular if the intermediate member is held on the support piece via a resilient connection.

The cam body can be formed as a ring.

It is advantageous if the cam body has recesses for accommodating a rotary tool, for example indentations provided on the edges and into which the projections of a rotary tool can engage with a positive fit.

As has already been mentioned, the mounting body can be part of a bone screw or of a hook; for example, the mounting body can be formed by a cylindrical shaft of a bone screw or of a hook.

A particularly advantageous configuration is one in which the mounting body is connected to a bone screw via a transverse support, the longitudinal axis of the bone screw extending parallel to the longitudinal axis of the mounting body and laterally offset from this longitudinal axis. Compared to a bone screw screwed into the bone, a transverse support of this kind provides an additional possibility of varying the position of the mounting body, that is to say the transverse support can be rotated on the bone screw and point in different angular positions or can be moved also in the axial direction, so that optimal adaptation to the anatomical circumstances is possible. It is advantageous in particular if the bone screw is rotatable about its longitudinal axis in the transverse support and can be secured in a defined angular position and/or in a defined axial position. This securing can preferably be effected by clamping.

According to a preferred embodiment of the invention, clamping in the transverse support can be provided for by a clamp piece which can be moved against the bone screw.

A particularly simple construction is obtained if, in order to move the clamp piece in the transverse support, a cam is mounted so that it engages against the clamp piece and is rotatable about a rotation axis. When this cam is rotated, it pushes the clamp piece into the clamping position, and the bone screw and the transverse support are no longer able to rotate relative to one another, but instead are fixedly connected to one another. Here too, the rotation movement of the cam can be limited, in particular by limit stops, so that overtightening is avoided and, in addition, maneuvering is made easier for the operating surgeon.

The rotation axis of the cam is preferably perpendicular to the plane of the transverse support.

The rotation axes of the cam in the transverse support and of the cam body can extend parallel to one another; in particular, these rotation axes can coincide.

The rotation axis of the cam and the longitudinal axis of the bone screw can be disposed parallel to one another, but it is also possible, in one particular embodiment, for the bone screw to be connected pivotably to the transverse support via a spherical connection, and for the clamp piece to be moved in the direction of a spherical engagement surface of the bone screw at the time of fixing. In this case, therefore, the bone screw can be pivoted relative to the rotation axis of the cam.

A particularly simple configuration is obtained if the transverse support has an elongate hole in which the bone screw, the clamp piece and the cam are accommodated. By rotating the cam, the latter and the bone screw are pressed against the edge of the elongate hole and clamped.

In a particularly preferred embodiment, the rotation axis of the cam and the longitudinal axis of the mounting body coincide.

For example, the mounting body can be a sleeve which is connected fixedly to the transverse support and through which a tool can be inserted for turning the cam.

It is advantageous if the sleeve has seats for a stabilizing tool.

The cam can, for example, be a ring which is rotatable in the transverse support and which is disposed at the transverse support end of the mounting body. In another embodiment, the cam is disposed on a core which is mounted rotatably in the sleeve and which, at least along part of its length, extends inside the sleeve.

In another embodiment, the mounting body is rotatable about its longitudinal axis in the transverse support and itself carries the cam. In such a configuration, it is in any case necessary to secure the rotary connection between transverse support and bone screw, by tensioning the cam, before rotating the cam body, disposed rotatably on the mounting body itself, into the tensioning position in order to tighten the clamping jaws.

The cam can be secured in the axial direction in the transverse support.

BRIEF DESCRIPTION OF THE DRAWINGS

The invention is explained in more detail in the following description of preferred embodiments and with reference to the drawings in which:

FIG. 8 shows a perspective view of the fixation device from FIG. 1 with the clamping jaws taken off and turned through 90° before being put back on;

DETAILED DESCRIPTION

Figures 1, 2:
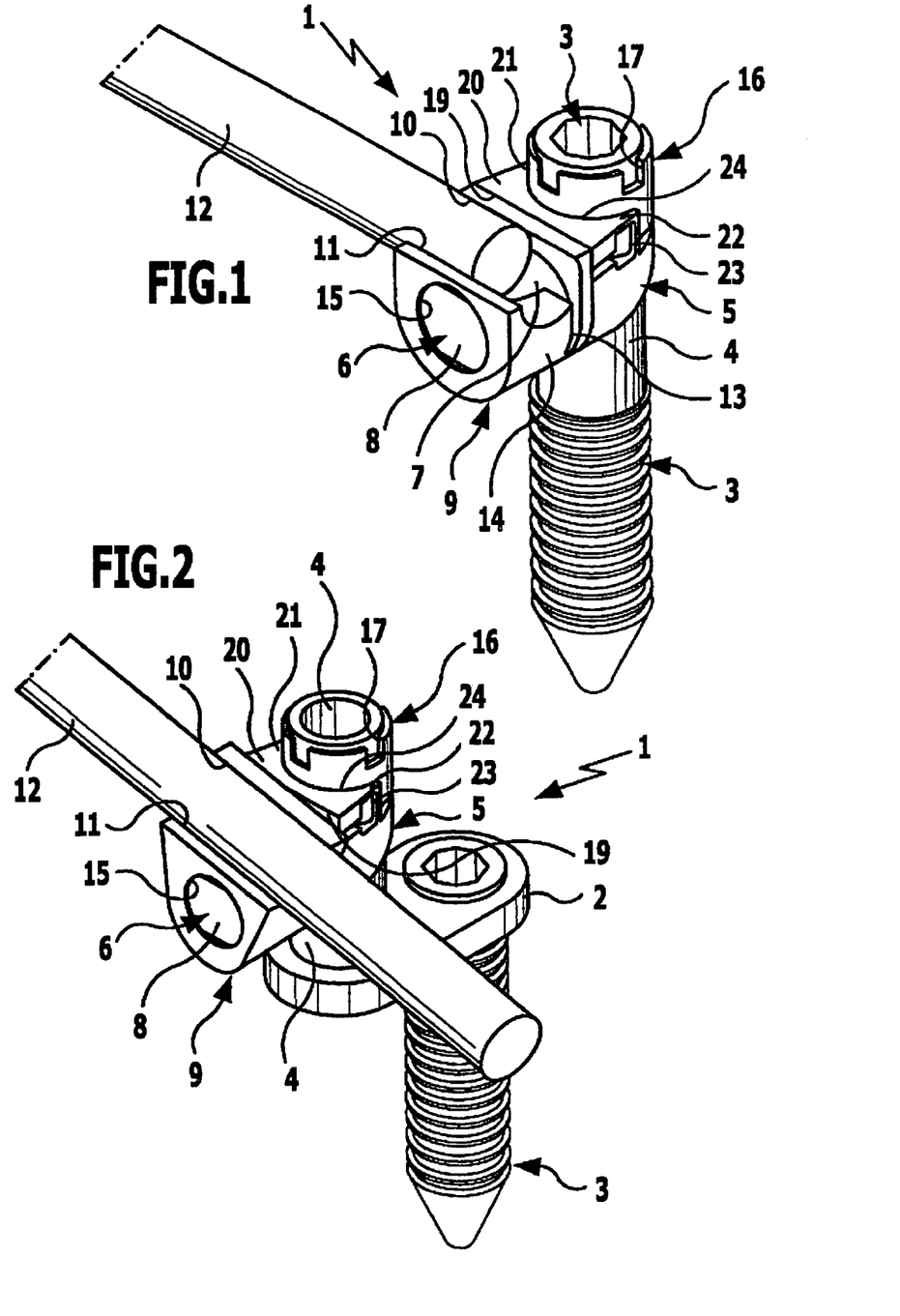
FIG. 1 shows a perspective view of an orthopedic fixation device with a rod-like fixation element and a clamping device for securing this rod-like fixation element on the shaft of a bone screw.
FIG. 2 shows a view similar to FIG. 1, with a transverse support between fixation device and bone screw.

The orthopedic fixation device 1 shown in FIGS. 1 to 8 is, in the illustrative embodiment in FIG. 1, fitted onto the shaft of a bone screw 3 whereas, in the illustrative embodiment in FIG. 2, it is fitted onto a sleeve-shaped, cylindrical mounting body 4 which is disposed on the bone screw 3 in a laterally offset position by way of a transverse support 2. In the following description, both the shaft of the bone screw 3 and the cylindrical mounting body 4 of the transverse support 2 are referred to jointly as mounting body 4, although it will be appreciated that the described orthopedic fixation device 1 can be fitted onto a wide variety of pin-shaped, shaft-shaped or sleeve-shaped mounting bodies.

A support piece 5 is pushed onto the mounting body 4 from above, tightly surrounds the mounting body 4 and is freely rotatable thereon. This support piece 5 has a mounting shaft 6 which protrudes from it in a direction transverse to the longitudinal direction of the mounting body 4 and which, along its length, has a peripheral groove 7 of arc-shaped cross-section and which, at its free end, terminates in an annular flange 8 flattened on opposite sides.

Figures 3, 4:
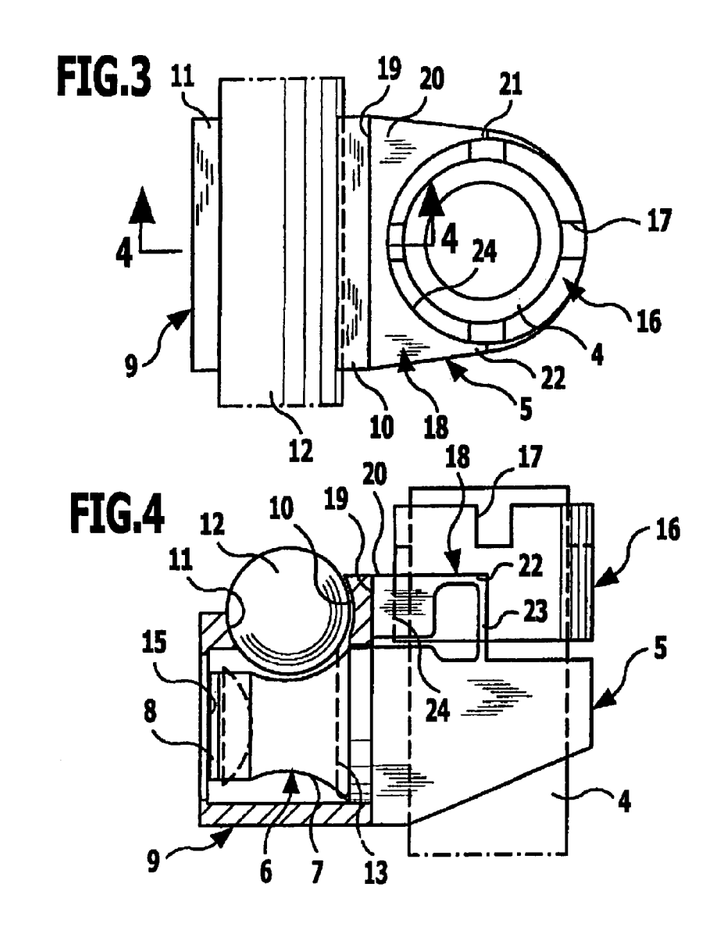
FIG. 3 shows a plan view of the clamp part of the fixation device shown in FIG. 1, with the clamping jaws not tightened relative to one another.
FIG. 4 shows a sectional view along line 4-4 in FIG. 3.
Figure 5:
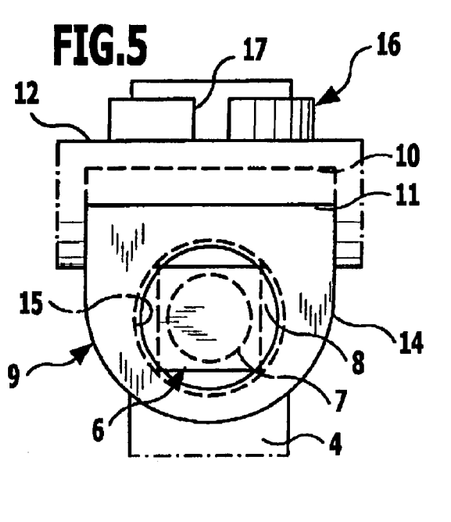
FIG. 5 shows a side view of the clamping device from FIG. 4.
Figures 6, 7:
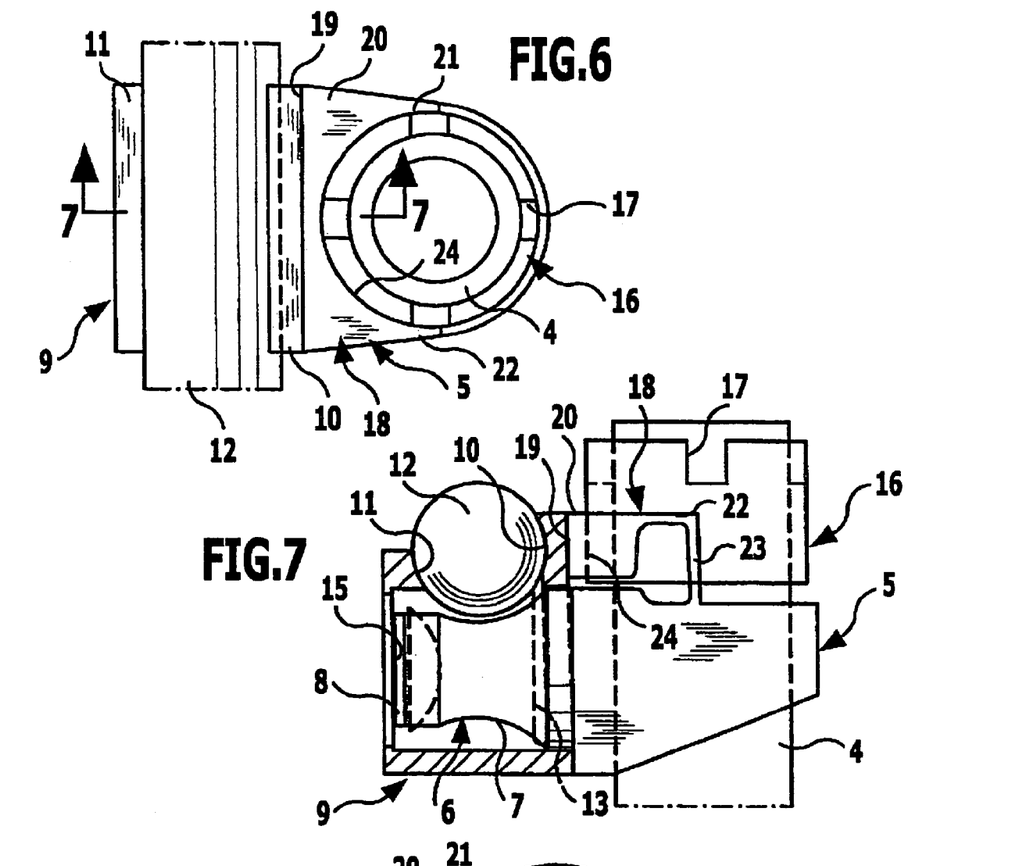
FIG. 6 shows a view similar to FIG. 3, with the clamping jaws tightened.
FIG. 7 shows a sectional view along line 7-7 in FIG. 6.
Figure 8:
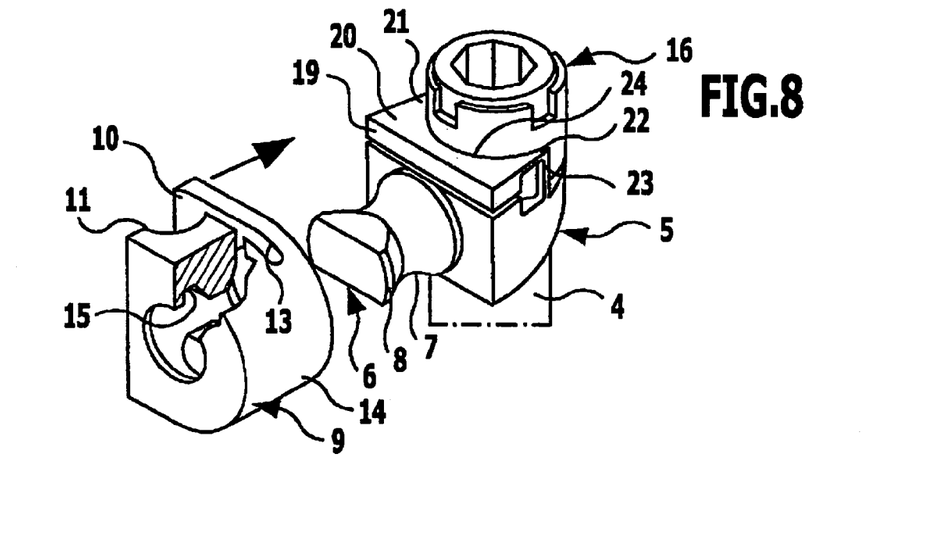

A substantially U-shaped clamping body 9 is pushed onto this mounting shaft 6, with two side walls which extend substantially parallel to one another and form two clamping jaws 10, 11. For this purpose, the side walls, in the region above the mounting shaft 6, are shell-shaped on the mutually facing sides, so that they can accommodate between them a rod-like fixation member 12 which is disposed transverse to the longitudinal direction of the mounting shaft 6. The two clamping jaws 10 and 11 are made resilient with respect to one another by an incision 13 formed in the cross-piece 14 of the clamping body 9 connecting them, so that the fixation member 12 can be snapped in elastically from above between the two clamping jaws 10, 11. In this snapped-in state, the fixation member dips into the peripheral groove 7 of the mounting shaft 6 (FIG. 4).

Extending through the clamping body 9 there is a continuous bore 15 which accommodates the mounting shaft 6 and thus bearingly supports the clamping body 9 so that it can rotate about the mounting shaft 6. The annular flange 8 of the mounting shaft 6 engages against the outside of the clamping body 9 and thus prevents removal of the clamping body 9 from the mounting shaft 6.

The bore 15 is configured in such a way that, when the clamping body 9 is rotated through 90° relative to the support piece 5, the clamping body 9 can be removed from the mounting shaft 6, this being made possible by the lateral flattenings on the annular flange 8 of the mounting shaft 6. A bayonet-like lock is thus obtained; by means of a deformation of the annular flange after attachment of the clamping body 9, the clamping body 9 can be secured on the mounting shaft 6 in a way which is permanent and prevents removal.

A ring surrounding the mounting body 4 is mounted rotatably on said mounting body 4 above the support piece 5, its outer circumference being eccentric with respect to the rotation axis defined by the mounting body 4, this ring thus forming a cam body 16. This cam body 16 is provided at its upper edge with axial incisions 17 into which a rotary tool (not shown in the drawing) can engage so that the cam body 16 can be rotated about the mounting body 4.

Fitted between the cam body 16 and the adjoining clamping jaw 10 there is a substantially U-shaped intermediate piece 18 which engages, with the outside 19 of its connecting cross-piece 20, on the clamping jaw 10, while the two branches 21, 22 adjoining the connecting cross-piece 20 merge into resilient webs 23 which extend parallel to the mounting body 4 and connect the intermediate piece 18 to the support piece 5. These resilient webs 23 permit a slight resilient movement of the intermediate piece 18 in the direction of the clamping jaws 10 and 11.

The branches 21 and 22 form a substantially semicircular internal engagement surface 24 surrounding the cam body 16.

In a release position, the cam body 16 protrudes to the least extent in the direction of the clamping jaws 10, 11. However, if the cam body 16 is turned, its periphery moves increasingly in the direction of the clamping jaws 10, 11 and in so doing moves the intermediate piece 18 in the direction of the clamping jaws 10, 11. In this way, the clamping jaw 10, designated below as the movable clamping jaw, is moved in the direction of the opposite clamping jaw 11, designated below as the stationary clamping jaw. The movable clamping jaw 10 engages against the rod-like fixation member 12 and moves the latter in the direction of the stationary clamping jaw 11, the clamping body 9 at the same time being pressed against the annular flange 8. The cam body 16 thus engages against the mounting body 4 and, as a result of this tensioning or loading of the cam body 16, all degrees of freedom of the described device are locked by clamping. As a result of the firm engagement on the annular flange 8, the clamping body 9 is fixed against rotation about the axis of the mounting shaft 6, the fixation member 12 is secured between the two mutually tightened clamping jaws 10, 11, and the support piece 5 is secured against rotation about the mounting body 4 by the engagement of the cam body 16 on the mounting body 4. Thus, simply by rotating the cam body 16, it is possible to secure four different degrees of freedom of the described configuration. It is of importance in this respect that this securing can be done from above and, similarly, the fixation member 12 can be inserted by snapping it from above in between the as yet untightened clamping jaws 10, 11. Thus, all the important steps involved in assembling and fixing the fixation device 1 can be performed by the operating surgeon from above through a very small access opening.

Figure 9:
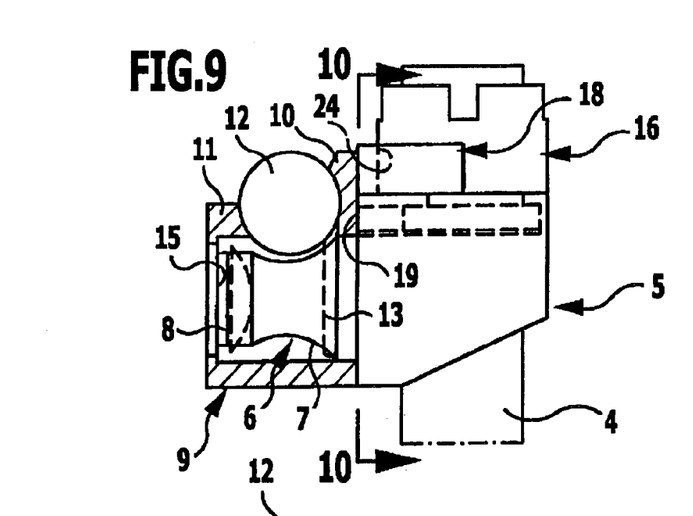
FIG. 9 shows a view similar to FIG. 4 in a modified illustrative embodiment of a fixation device with a freely movable intermediate piece.
Figure 10:
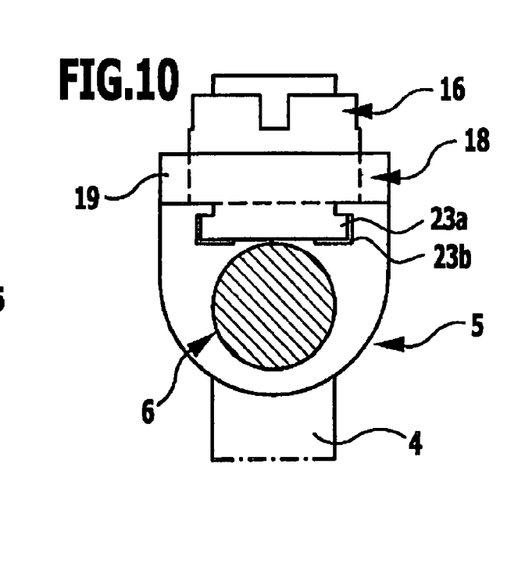
FIG. 10 shows a sectional view along line 10-10 in FIG. 9.
Figure 11:
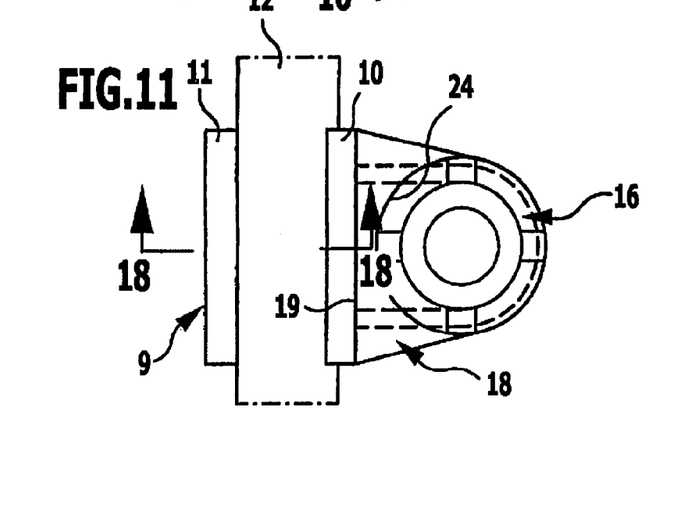
FIG. 11 shows a plan view of the fixation device from FIG. 9.

In the illustrative embodiment in FIGS. 9 to 11, a similar construction is chosen. Corresponding parts therefore carry the same reference numbers. In contrast to the illustrative embodiment in FIGS. 1 to 8, the intermediate piece 18 is not connected by resilient webs to the support piece 5 and instead is completely separate from this. The intermediate piece 18, however, engages with a flange-like widening 23a in a guide groove 23b extending parallel to the clamping direction of the clamping jaws 10, 11, so that the intermediate piece 18 is guided longitudinally displaceably in the support piece 5. In this way, greater movements of the intermediate piece can also be effected, which could possibly lead to excessive bending of the resilient webs 23.

Figure 12:
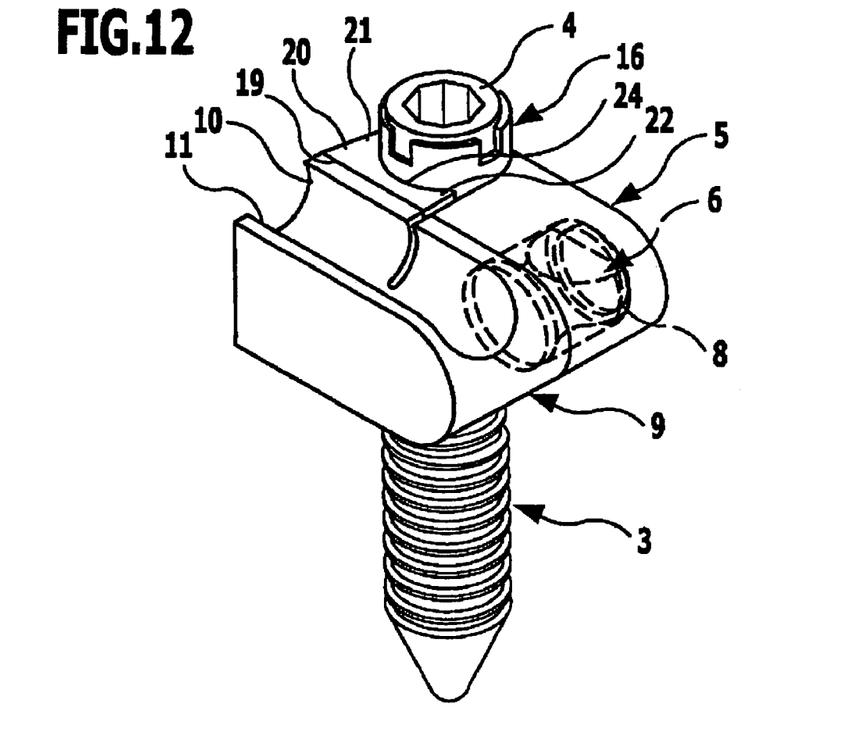
FIG. 12 shows a perspective view of a modified illustrative embodiment of a fixation device with a pivot axis next to the eccentric axis.

In the illustrative embodiment in FIG. 12, a similar construction to the one in the illustrative embodiment in FIG. 1 is chosen, but the mounting shaft 6 has here been shifted to a position laterally alongside the bone screw 3, the cam body 16 and the intermediate piece 18, and, in the illustrative embodiment shown, the mounting shaft 6 is not disposed on the support piece 5 but instead on the clamping body 9 and protrudes into a corresponding receiving bore in the support piece 5. These are modifications which can be adopted individually or in combination and lead to different geometries of the overall configuration, but in principle do not change anything.

Figure 13:
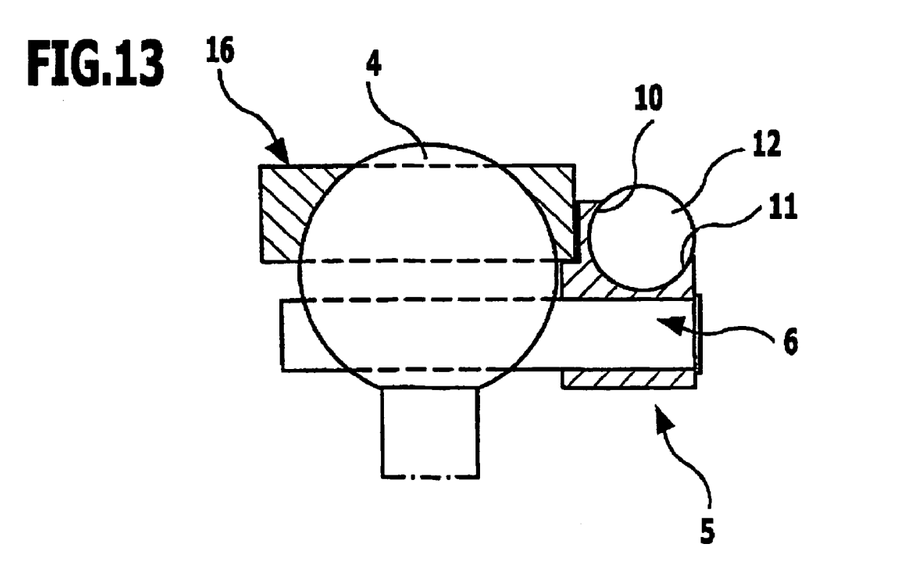
FIG. 13 shows a schematic sectional view through a further preferred illustrative embodiment of a fixation device with spherical pivotability.

In the illustrative embodiment in FIG. 13, which is represented only very schematically and in which parts corresponding to the above-described embodiments carry the same reference numbers, a spherical mounting body 4 is used, for example a spherical head on a bone screw. In this way, the whole fixation device is not only mounted on the bone screw to be rotatable about an axis, it can also be pivoted in other directions and then clamped on the spherical head of the mounting body 4 by the cam body 16.

Figure 14:
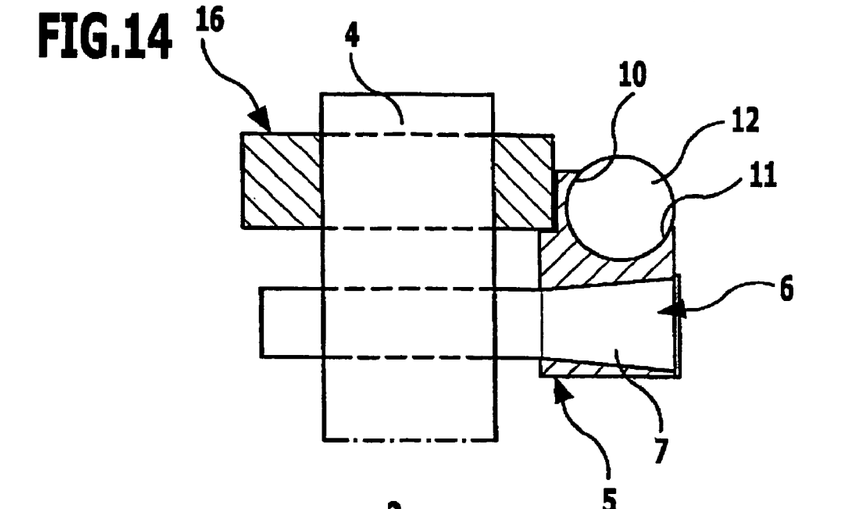
FIG. 14 shows a schematic longitudinal section through a further preferred illustrative embodiment of a fixation device with a cone-shaped limit stop for the clamping jaws.
Figure 15:
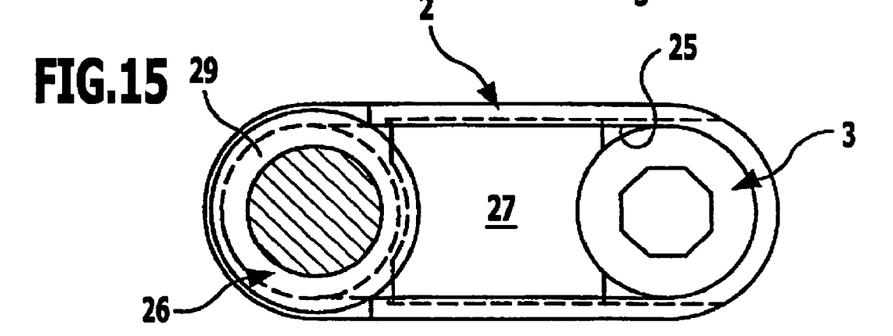
FIG. 15 shows a plan view of a transverse support for connection of fixation device and a bone screw, with a cam-type clamping means in the released state.
Figure 16:
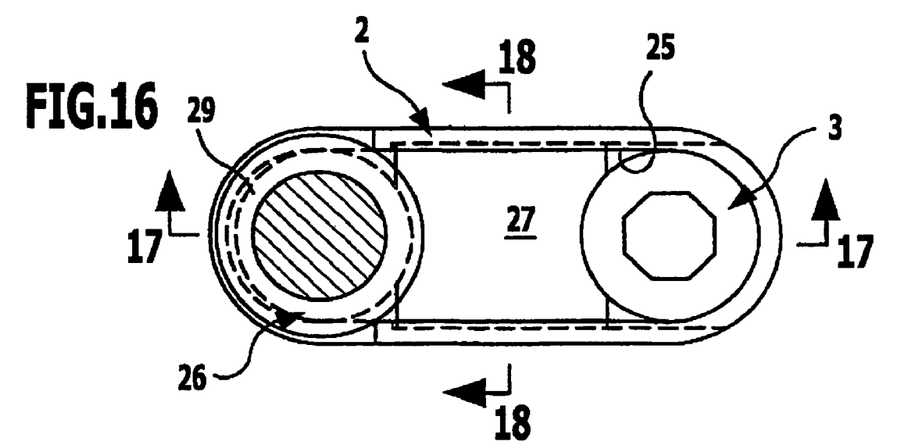
FIG. 16 shows a view similar to FIG. 15, with the cam tensioned.
Figure 17:
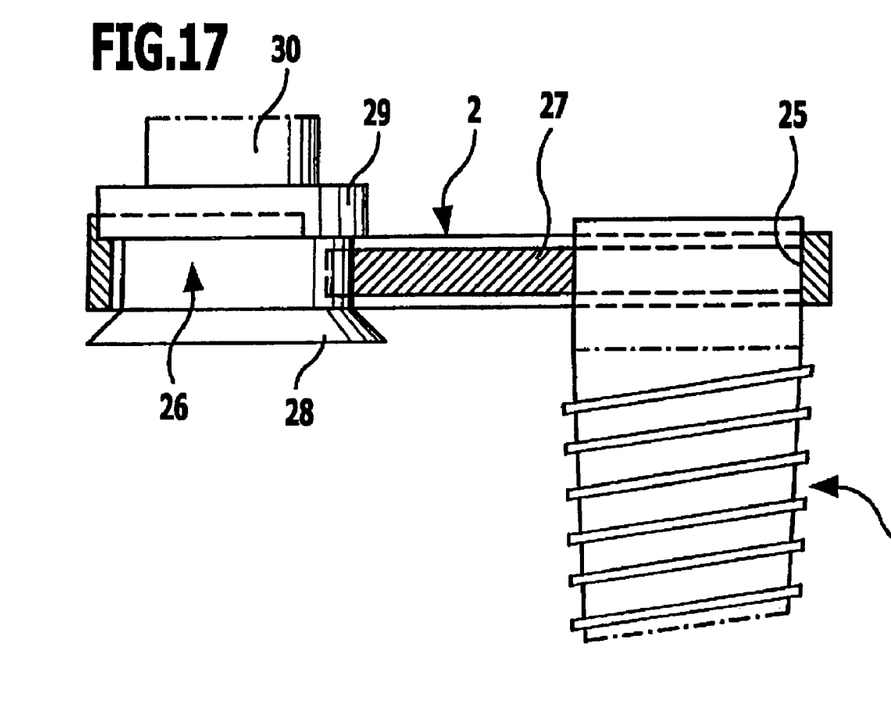
FIG. 17 shows a sectional view along line 17-17 in FIG. 16.
Figure 18:
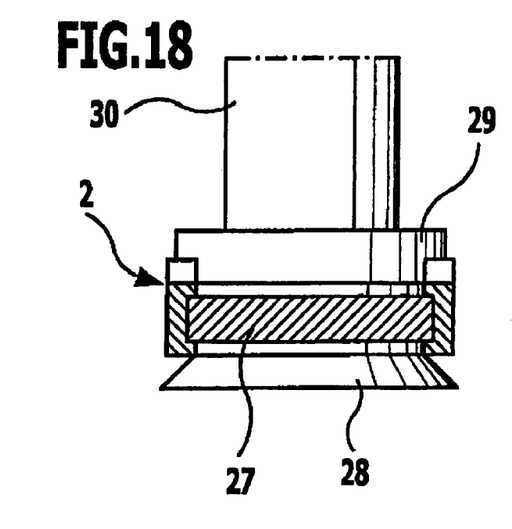
FIG. 18 shows a sectional view along line 18-18 in FIG. 16.

In the illustrative embodiment in FIG. 14, in which corresponding parts once again carry the same reference numbers, the mounting shaft 6 has a conical configuration so that, when the cam body 16 is tensioned, the clamping body 9 is pressed against the conically increasingly thicker end of the mounting shaft 6 and is thus secured.

In the illustrative embodiment in FIG. 2, the fixation device is held on the bone screw 3 via a transverse support 2. In a preferred illustrative embodiment of such a transverse support 2, as is shown for example in FIGS. 15 to 18, this transverse support 2 is configured as a flat, strip-shaped plate and has an oblong hole 25 extending along a large part of its length. The bone screw 3 is passed through this oblong hole, and, in addition, a cam 26 is mounted rotatably at the opposite end of said oblong hole 25. Disposed between the bone screw 3 and the cam 26 there is a clamp piece 27 which is longitudinally displaceable in the oblong hole 25 and engages both against the bone screw 3 and also against the cam 26.

For the sake of clarity, the mounting body 4 is not shown in the illustration in FIGS. 15 to 18; this mounting body could, for example, be welded to the transverse support 2 and surround the cam 26.

In the released position, the periphery of the cam 26 is at a maximum spacing from the bone screw 3 and, when the cam 26 is rotated, this spacing becomes smaller, so that in this way the clamp piece 27 is moved in the direction of the bone screw 3 and finally braces the latter against the edge of the oblong hole 25 and thus connects the transverse support 2 fixedly to the bone screw 3. With the cam 26 released, the operating surgeon can therefore turn the transverse support 2 on the bone screw 3 to the desired position, and this position can be fixed simply by tensioning the cam 26.

This therefore affords an additional possibility of bringing the orthopedic fixation device shown in FIG. 2 into different positions relative to the bone screw 3, so that an especially wide range of possible engagement positions is obtained. In this case too, the cam 26 is actuated at the same place where the cam body 16 is actuated, since they are disposed coaxially with respect to one another, so that here too the movement possibilities can be obtained through the same very small access opening.

Figure 19:
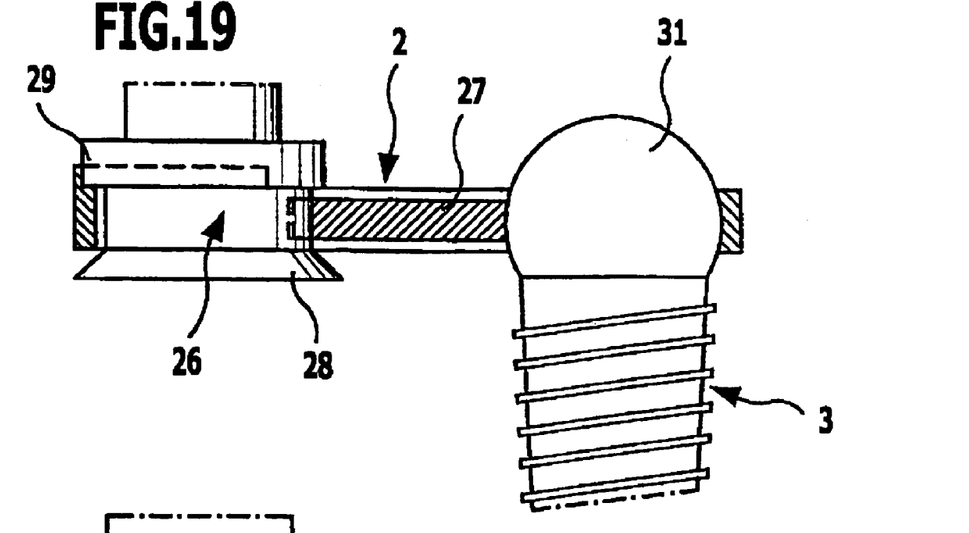
FIG. 19 shows a view similar to FIG. 17, with the device mounted on a spherical bone screw head.

In the illustrative embodiment in FIGS. 15 to 18, the bone screw 3 has a cylindrical outer shaft in the region of the transverse support 2, whereas in the illustrative embodiment in FIG. 19, which is otherwise of the same construction, the bone screw 3 has a spherical configuration in this region and is held between the clamp piece 27 on the one hand and the transverse support 2 on the other hand so as to be axially immovable, but free to pivot. When the clamp piece 27 is moved against this spherical engagement surface 31 upon tensioning of the cam 26, the different pivot direction of the bone screw 3 in the transverse support 2 is thus also permanently fixed.

Figure 20:
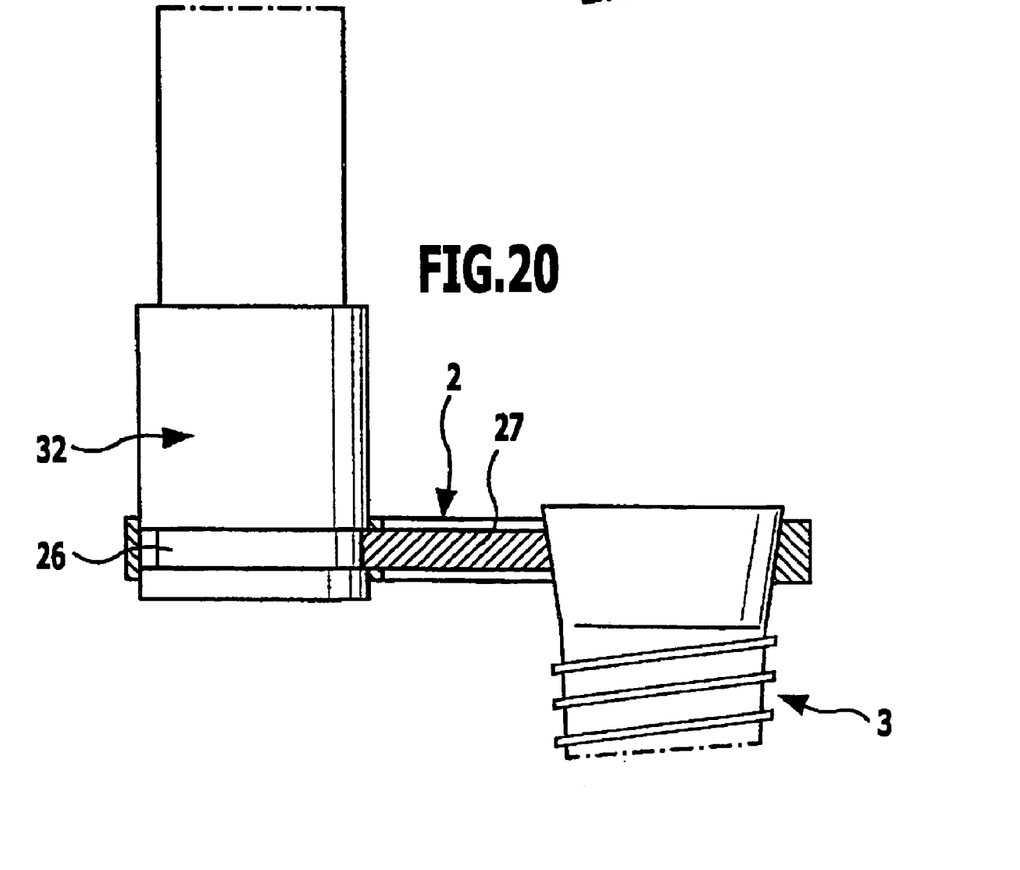
FIG. 20 shows a view similar to FIG. 19, with the device mounted on a conical bone screw head.

The illustrative embodiment in FIG. 20 largely corresponds to that in FIGS. 15 to 18, and corresponding parts therefore carry the same reference numbers. Whereas the cam 26 in the illustrative embodiment in FIGS. 15 to 18 has an annular configuration, the illustrative embodiment in FIG. 20 shows a cam 16 in the form of a rotatable core 32 which, in its lower region disposed in the transverse support 2, forms the cam 26. The core 32 can be turned by a tool connected to it from above with a positive fit.

Figure 21:
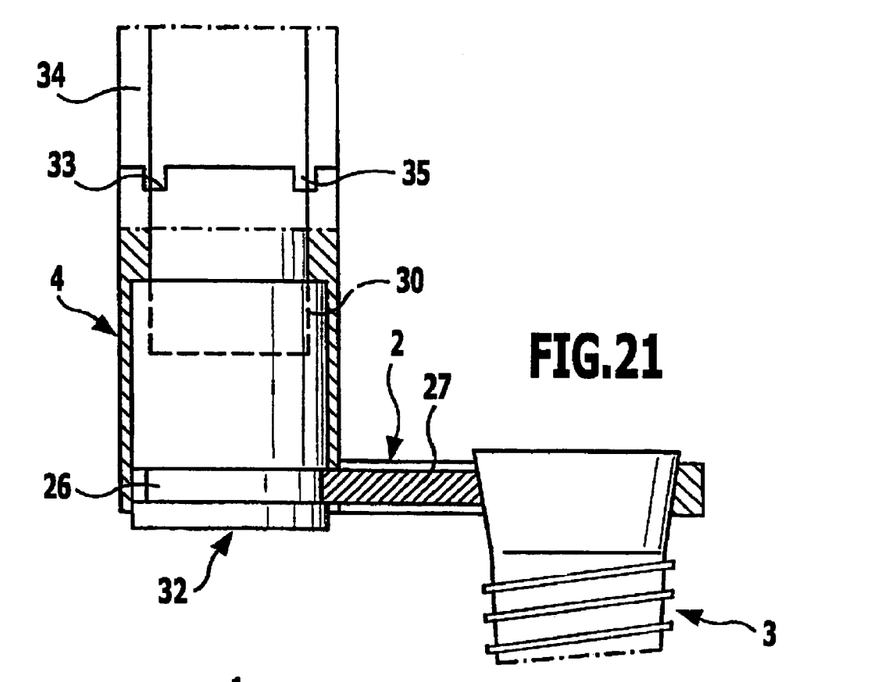
FIG. 21 shows a view similar to FIG. 20 in another preferred illustrative embodiment with a cam in the form of a rotatable core and with a mounting body which surrounds this core and is fixedly connected to the transverse support.
Figure 22:
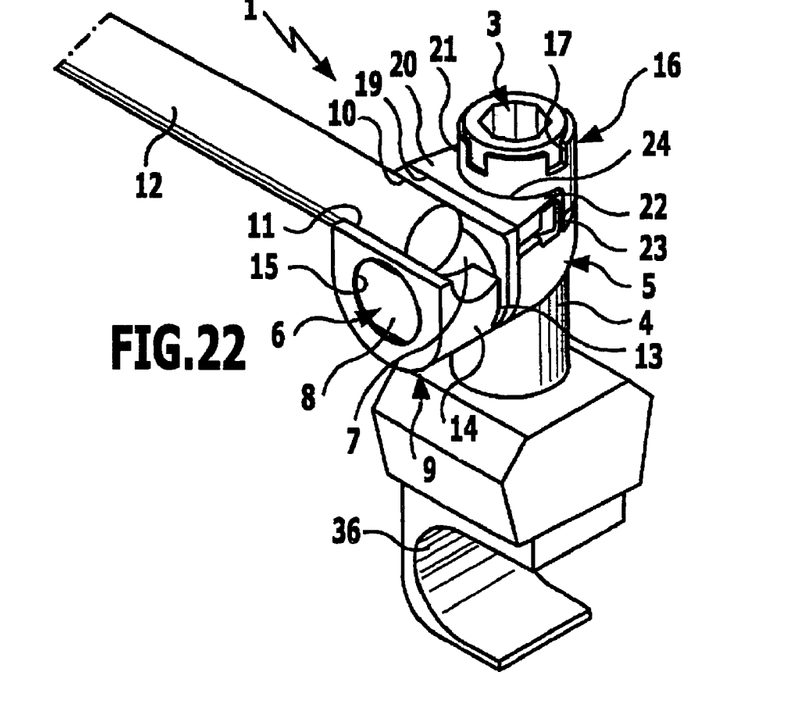
FIG. 22 shows a view similar to FIG. 1, with a hook instead of a bone screw.

The core 32 can itself form the mounting body 4 on which the fixation device 1 is secured, but provision can also be made for the mounting body 4 to be formed as a sleeve connected fixedly to the transverse support 2, as is shown in the illustrative embodiment in FIG. 21 which otherwise corresponds to the illustrative embodiment in FIG. 20. To rotate the core 32, a rotary tool 30 can engage in the interior of the hollow mounting body 4. It is also expedient if, in addition, a stabilizing tool 34 is provided, for example in the form of a sleeve which is fitted onto the mounting body 4 and which, with projections 35, engages with a positive fit into corresponding recesses 33 of the mounting body 4. In this way it is possible, without transmitting torques to the transverse support 2, to rotate the core 32 relative to the mounting body 4 and thus bring the cam 26 into the tightening or tensioning position.

The bone screw 3 in the illustrative embodiments described above can also be replaced by a hook 36 which engages round an osseous structure. By means of a shaft-like upper part, this hook can also carry a transverse support 2 or a support piece 5, in the same way as the bone screw, the only difference being that the connection to the bone is in this case effected not by a thread, but instead by a hook-shaped end. This modification is possible in all of the illustrative embodiments described above.

What is claimed is:

1. Orthopedic fixation device for securing a rod-like fixation element, comprising:
   two clamping jaws movable relative to one another and which, when brought together, clamp the fixation element between them, and
   an eccentric cam body mounted on the fixation device adjacent the clamping jaws, said eccentric cam body being rotatable about a rotation axis and which, when rotated, pushes one clamping jaw toward the other clamping jaw in a radial direction with respect to said rotation axis.

2. Device according to claim 1, wherein the cam body is mounted rotatably on a rotationally symmetrical mounting body on which the clamping jaws are also held.

3. Device according to claim 2, wherein the rotation axis of the cam body extends parallel to an axis of the rotationally symmetrical mounting body.

4. Device according to claim 3, wherein the rotation axis of the cam body is identical to the axis of the rotationally symmetrical mounting body.

5. Device according to claim 2, wherein the rotationally symmetrical mounting body has a circular cylinder configuration.

6. Device according to claim 2, wherein the rotationally symmetrical mounting body has a spherical configuration.

7. Device according to claim 2, wherein the rotationally symmetrical mounting body has a conical configuration.

8. Device according to claim 2, wherein a support piece, which carries the two clamping jaws, is held on the rotationally symmetrical mounting body.

9. Device according to claim 8, wherein the support piece is rigidly connected to the mounting body.

10. Device according to claim 8, wherein the support piece is held on the rotationally symmetrical mounting body so as to be rotatable about an axis of symmetry of said mounting body.

11. Device according to claim 10, wherein the support piece can be pushed onto the rotationally symmetrical mounting body in a direction of the axis of symmetry.

12. Device according to claim 8, wherein the clamping jaws are connected to the support piece so as to be able to pivot about a rotation axis extending parallel to a clamping direction of the clamping jaws.

13. Device according to claim 12, wherein the rotation axis of the clamping jaws and the rotation axis of the cam body are located in one plane.

14. Device according to claim 12, wherein the rotation axis of the clamping jaws and the rotation axis of the cam body are laterally offset from one another.

15. Device according to claim 12, wherein:
   both clamping jaws are formed by side walls of a clamping body which has a U-shaped cross-section, and
   said side walls can be bent resiliently relative to one another.

16. Device according to claim 12, wherein a pivot connection between the clamping jaws and the support piece is releasable.

17. Device according to claim 16, wherein the pivot connection comprises two mounting members which engage behind one another in a bayonet fashion and which, in a defined angular position, do not engage behind one another such that they are then axially movable relative to one another.

18. Device according to claim 2, wherein the cam body is formed as a ring.

19. Device according to claim 2, wherein the mounting body is part of a bone screw.

20. Device according to claim 2, wherein the mounting body is part of a hook.

21. Device according to claim 2, wherein the mounting body is connected to a bone screw or a hook via a transverse support, and in that a longitudinal axis of the bone screw or of the hook extends laterally offset from a longitudinal axis of the mounting body.

22. Device according to claim 21, wherein the bone screw or the hook is rotatable about its longitudinal axis in the transverse support and can be clamped in a defined angular position.

23. Device according to claim 22, wherein, in order to permit clamping in the transverse support, a clamp piece can be moved against the bone screw or the hook.

24. Device according to claim 23, wherein, in order to move the clamp piece in the transverse support, a cam is mounted so that it engages against the clamp piece and is rotatable about a rotation axis.

25. Device according to claim 24, wherein the rotation axis of the cam is perpendicular to a plane of the transverse support.

26. Device according to claim 25, wherein the rotation axis of the cam extends parallel to the longitudinal axis of the bone screw or of the hook.

27. Device according to claim 25, wherein the bone screw or the hook is connected pivotably to the transverse support via a spherical connection, and the clamp piece can be moved in a direction of a spherical engagement surface of the bone screw or of the hook at the time of fixing.

28. Device according to claim 23, wherein the transverse support has an elongate hole in which the bone screw or the hook, the clamp piece and the cam are accommodated.

29. Device according to claim 24, wherein the rotation axes of the cam in the transverse support and of the cam body extend parallel to one another.

30. Device according to claim 29, wherein the rotation axes of the cam and of the cam body coincide.

31. Device according to claim 24, wherein the rotation axis of the cam and the longitudinal axis of the mounting body coincide.

32. Device according to claim 31, wherein the mounting body is a sleeve which is connected fixedly to the transverse support and through which a tool can be inserted for turning the cam.

33. Device according to claim 32, wherein the mounting body has seats for a stabilizing tool.

34. Device according to claim 32, wherein the cam is a ring which is rotatable in the transverse support and which is disposed at the transverse support end of the mounting body.

35. Device according to claim 32, wherein the cam is disposed on a core which is mounted rotatably in the mounting body and which, at least along part of its length, extends inside the mounting body.

36. Device according to claim 31, wherein the mounting body is rotatable about its longitudinal axis in the transverse support and itself carries the cam.

37. Device according to claim 24, wherein the cam is secured in an axial direction in the transverse support.

38. Device according to claim 1, wherein:
 a first of the two clamping jaws is configured as a clamping jaw whose spacing from the rotation axis of the cam body is substantially fixed, and
 a second of the two clamping jaws is configured as a movable clamping jaw which can be moved by the cam body toward the first clamping jaw.

39. Device according to claim 38, wherein the first clamping jaw is connected rigidly to a support piece.

40. Device according to claim 39, further comprising an intermediate member between the cam body and the clamping jaws which, when the cam body is rotated, is moved against the clamping jaws.

41. Device according to claim 38, wherein a limit stop for the first clamping jaw is disposed on a support piece and limits a movement of the first clamping jaw in a clamping direction of the clamping jaws and thus limits a movement of the first clamping jaw away from the rotation axis of the cam body.

42. Device according to claim 38, wherein the clamping jaws are connected to a support piece so as to be able to pivot about a rotation axis extending parallel to a clamping direction of the clamping jaws.

43. Device according to claim 38, further comprising an intermediate member between the cam body and the clamping jaws which, when the cam body is rotated, is moved against the clamping jaws.

44. Device according to claim 38, wherein, when the cam body is released, the clamping jaws can be moved so far apart from one another that a rod-like fixation element can be snap-fitted in between them.

45. Device according to claim 1, wherein a limit stop for a first clamping jaw is disposed on a support piece and limits a movement of the first clamping jaw in a clamping direction of the clamping jaws and thus limits a movement of the first clamping jaw away from the rotation axis of the cam body.

46. Device according to claim 45, wherein the clamping jaws are connected to the support piece so as to be able to pivot about a rotation axis extending parallel to the clamping direction of the clamping jaws.

47. Device according to claim 1, further comprising an intermediate member between the cam body and the clamping jaws which, when the cam body is rotated, is moved against the clamping jaws.

48. Device according to claim 47, wherein the intermediate member is held movably on a support piece.

49. Device according to claim 48, wherein the intermediate member is held on the support piece via a resilient connection.

50. Device according to claim 1, wherein, when the cam body is released, the clamping jaws can be moved so far apart from one another that a rod-like fixation element can be snap-fitted in between them.

51. Device according to claim 1, wherein the cam body has recesses for accommodating a rotary tool.

* * * * *

UNITED STATES PATENT AND TRADEMARK OFFICE
CERTIFICATE OF CORRECTION

PATENT NO. : 7,591,838 B2
APPLICATION NO. : 11/070826
DATED : September 22, 2009
INVENTOR(S) : Kramer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1123 days.

Signed and Sealed this

Twenty-first Day of September, 2010

David J. Kappos
*Director of the United States Patent and Trademark Office*